United States Patent
Norris et al.

(10) Patent No.: US 6,529,273 B1
(45) Date of Patent: Mar. 4, 2003

(54) MONITORING OIL FILMS

(75) Inventors: John Oliver Wilson Norris, Abingdon (GB); Allan Peter Smith, Abingdon (GB)

(73) Assignee: Accentus plc, Didcot (GB)

( * ) Notice: Subject to any disclaimer, the term of this patent is extended or adjusted under 35 U.S.C. 154(b) by 0 days.

(21) Appl. No.: 09/508,050

(22) PCT Filed: Sep. 18, 1998

(86) PCT No.: PCT/GB98/02837

§ 371 (c)(1),
(2), (4) Date: Mar. 7, 2000

(87) PCT Pub. No.: WO99/15881

PCT Pub. Date: Apr. 1, 1999

(30) Foreign Application Priority Data

Sep. 19, 1997 (GB) .............................................. 9719856

(51) Int. Cl.$^7$ .............................. G01B 11/06; H01J 3/14
(52) U.S. Cl. ........................ 356/381; 356/417; 356/630; 356/70; 250/237
(58) Field of Search ................................. 356/381, 317, 356/318, 417, 630, 70; 250/458.1, 459.1, 461.1, 462.1, 201.3, 310, 237, 226; 73/40; 436/518; 378/45

(56) References Cited

U.S. PATENT DOCUMENTS

| | | | | |
|---|---|---|---|---|
| 4,983,817 A | * | 1/1991 | Dolash et al. | 250/226 |
| 5,001,353 A | * | 3/1991 | Odake et al. | 250/461.1 |
| 5,455,422 A | * | 10/1995 | Anderson et al. | 250/226 |
| 5,541,413 A | * | 7/1996 | Pearson et al. | 250/339.11 |
| 5,754,620 A | * | 5/1998 | Hossain et al. | 378/45 |
| 5,926,270 A | * | 7/1999 | Longacre | 356/318 |
| 5,936,728 A | * | 8/1999 | Bouzid | 356/417 |
| 5,963,310 A | * | 10/1999 | Brown et al. | 356/347 |
| 5,974,860 A | * | 11/1999 | Kuroda et al. | 356/318 |
| 6,141,096 A | * | 10/2000 | Stern et al. | 356/417 |
| 6,173,036 B1 | * | 1/2001 | Hossain et al. | 378/45 |

FOREIGN PATENT DOCUMENTS

| JP | 06 174 431 | * | 6/1994 |
|---|---|---|---|
| JP | 406214162 | * | 8/1994 |

* cited by examiner

Primary Examiner—Frank G. Font
Assistant Examiner—Sang H. Nguyen
(74) Attorney, Agent, or Firm—William H. Holt

(57) ABSTRACT

The thickness of an organic material on a substrate, such as an oil film on a metal sheet (12), is monitored by illuminating the film with ultraviolet radiation (14) and measuring the fluorescent light intensity (44, 48) from the organic material. The reflectivity of the substrate is also monitored, and used in calculating the thickness. The technique is also applicable where the substrate is moving.

12 Claims, 2 Drawing Sheets

MONITORING OIL FILMS

This invention relates to a method and an apparatus for monitoring the thickness of an organic material, such as an oil film, on a surface of a substrate, for example on material in a rolling mill, using fluorescence.

The use of fluorescence from an oil film to detect the film or to monitor its thickness is known, for example from U.S. Pat. No. 4,956,558 (Batishko et al.) in which optical fibres are used to monitor fluorescence from lubricating oil illuminated by ultraviolet light; the measurements can be calibrated by observing the fluorescent intensity with films of known thickness. WO 93/22655 (Thiokol Corp.) describes apparatus for detecting contamination such as grease on a surface, using a light beam incident on the surface, and a tunable filter to monitor light reflected or scattered from the surface at a wavelength corresponding to an optical property of the material. One such optical property is fluorescence, and the measurements can be calibrated by inspecting a surface known not to fluoresce, so as to obtain a baseline or zero signal level. In DE 3038107 A (Keck et al.) a fluorescence technique is used to monitor for oil contamination on water, the incident light beam being pulsed and the detector being sensitive to that frequency, so that stray light from other sources does not affect measurements.

In hot metal rolling, whether of ferrous or non-ferrous metals, lubrication by a rolling oil in the bite of the rollers is believed to play an important role in the finish attained. An aim of the invention is to provide a way of monitoring and measuring the thickness of an oil film on a roller as it leaves the bite. Other applications are the measurement of oil film thickness applied to steel sheet in preparation for the automotive industry and the detection of residual oils. A problem with such measurements is that fluorescence intensities depend on the characteristics of the surface of the sheet, such as its reflectivity. This invention provides a scheme for compensating for these quantities.

According to the present invention there is provided a method of monitoring the thickness of oil on the surface of a metal substrate, the method comprising the steps of illuminating a region of the surface with radiation of a suitable wavelength to cause fluorescence in the oil, and detecting the intensity of the fluorescent radiation, characterized by also illuminating the same region of the surface at the same time with a reference beam that experiences negligible absorption when incident on the oil, and measuring the intensity of the reflected reference beam to provide a measure of the reflectivity of the surface, and determining the thickness of the oil at that region from both the values of the fluorescent intensity and the reflectivity of the surface.

The invention also provides such a method, characterized by also measuring the intensity of radiation reflected from the same region of the surface to provide a measure of the reflectivity of the surface, and determining the thickness of the oil at that region from both the values of the fluorecent intensity and the reflectivity of the surface, wherein the intensity of the fluorescent radiation is measured at two different wavelengths, in order to enable changes of temperature to be taken into account.

The invention also provides an apparatus for performing such a method.

The source of radiation to cause fluorescence desirably produces ultraviolet light, and the preferred source is a pulsed xenon flash lamp. This is desirably combined with a filter so the surface is only illuminated with suitable u-v wavelengths to cause fluorescence. Where there is a reference beam, it is preferably incident substantially normally to the surface.

For detecting the reflected radiation the preferred detector is a photodiode. In a preferred arrangement the intensities of both the reflected reference beam and the reflected fluorescence-causing radiation are detected. To detect the latter a photodiode is desirably combined with a filter similar to that used in the source.

The fluorescent radiation is of much lower intensity and may be detected by a photomultiplier or an intensified diode array, desirably combined with a filter to select only the desired fluorescent wavelengths. This filter might be replaced by a monochromator. If the radiation source is pulsed, then the fluorescent radiation detector is desirably gated in synchronisation with the pulses, so that the effect of any ambient light is suppressed.

The reflectivity of the surface of the substrate affects the intensity of the fluorescent light in two ways: a highly reflective surface reflects the incident radiation back through the organic layer, causing more fluorescence, and also reflects some of the fluorescent radiation that was initially travelling away from the collection optics. Measuring the reflected radiation enables these effects to be taken into account.

The invention will now be further and more particularly described, by way of example only, and with reference to the accompany drawings in which.

Figure 1:
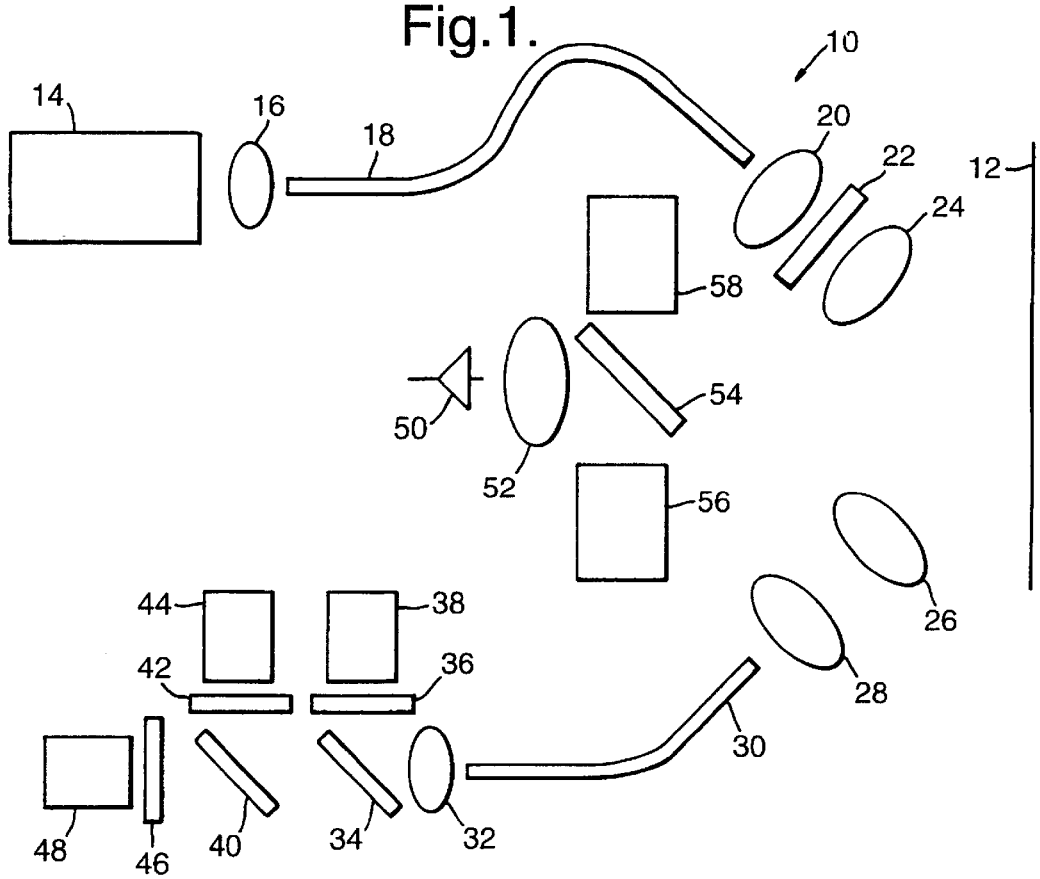
FIG. 1 shows a schematic diagram of an apparatus for monitoring oil thickness on a metal sheet.

Referring to FIG. 1, an apparatus 10 for measuring the thickness of oil on a metal sheet 12 during a rolling operation includes a xenon flash lamp 14 which operates at 8 Hz giving flashes of duration about 10 $\mu$s. The lamp 14 emits radiation in both the visible and ultraviolet parts of the spectrum. The radiation is focused using lens 16 into an optical fibre 18 to transmit it to the measurement region, and is then collimated using a lens 20 and passed through a type UG11 filter 22 to select ultraviolet wavelengths in the range about 290 nm to 370 nm. The filter 22 also removes any fluorescence generated in the transmission fibre 18. A lens 24 focuses the u-v radiation onto the sheet 12.

Scattered u-v and fluorescent light are collected by lens 26 and focused into a transmission fibre 30 using a lens 28. Output from the transmission fibre 30 is collected and focused onto three detectors 38, 44 and 48 by a lens 32. Beam splitter 34 deflects onto the detector 38 through a type UG11 transmission filter 36 any reflected u-v radiation that has been collected. Beam splitter 40 reflects a portion of the fluorescent light through a filter 42 onto the detector 44, the remainder of the fluorescence passing through a filter 46 onto the detector 48. The two fluorescence signals may be used to calculate oil temperature as well as film thickness. The filters 42 and 46 that are used will depend to a certain extent on the oil, but an example would be a 5 nm bandpass filter at 410 nm for filter 42 and an equivalent one centred at 385 nm for filter 46. The detectors 44 and 48 are gated to operate in synchronism with the 10 $\mu$s flashes emitted by the flash lamp 14.

The detector 48 could be a diode array incorporating 512 diodes. For some purposes it is preferable to replace the filter 46 with a monochromator (not shown) and remove the beam splitter 40; for example by using a monochromator which gives a dispersion of 70 nm over the diode array 48 the spectrum of the fluorescent light can be observed.

Figure 4:
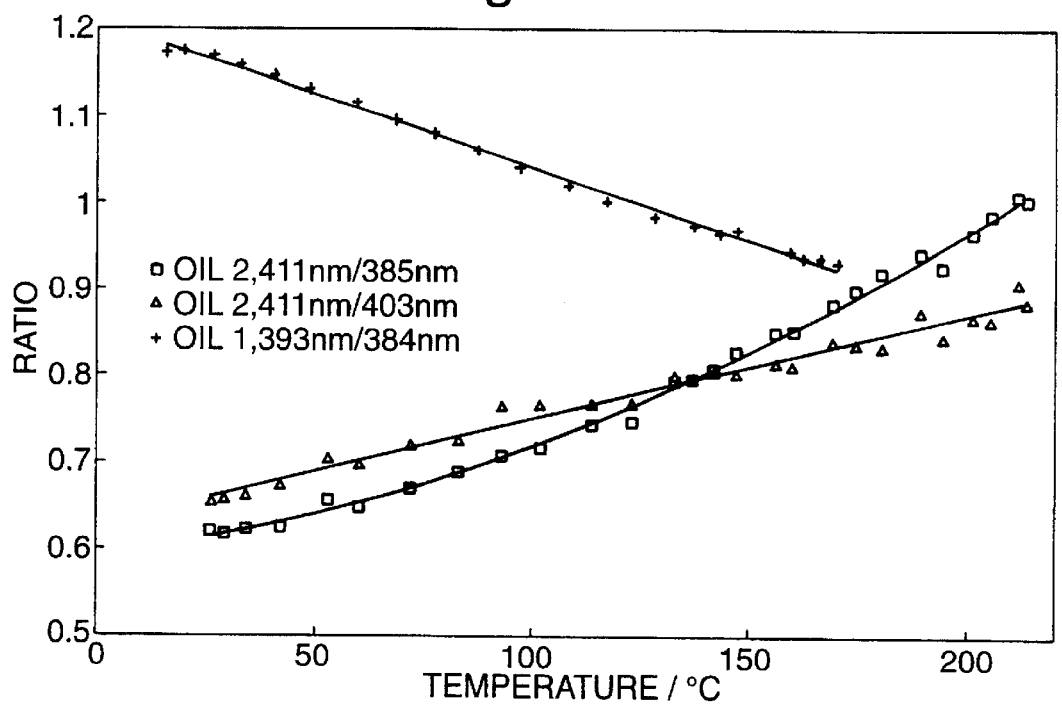
FIG. 4 shows graphically how the ratio of fluorescent light intensities at two specified wavelengths varies with temperature, for two different oils.

The detectors 44 and 48 are used to measure the intensity of the fluorescent light. This will depend upon the composition of the oil, and in some cases it may be found necessary to add a fluorescent component such as a rhodamine dye. However, rolling oils studied have been found to fluoresce without any such addition, possibly due to the presence of aromatic compounds. For example oils referred to as oil 1 and oil 2 were both found to have fluorescent peaks between 385 and 390 nm, and between 400 and 410 nm, though of different intensities. The intensity and the shape of the fluorescent spectrum of a particular oil also depend upon its temperature, but this can be taken into account by a calibration experiment for the oil in question, determining the temperature dependence of the oil fluorescence intensity, and measuring the temperature of the oil during operation. This may be done by monitoring two appropriate regions of the fluorescent spectrum and measuring the ratio between the intensities at the two wavelengths. As shown in FIG. 4, these ratios can vary smoothly with temperature; the graph shows the ratio between 393 nm and 384 nm for oil 1, and the ratios between 411 nm and 385 nm and between 411 nm and 403 nm for oil 2.

Figure 2:
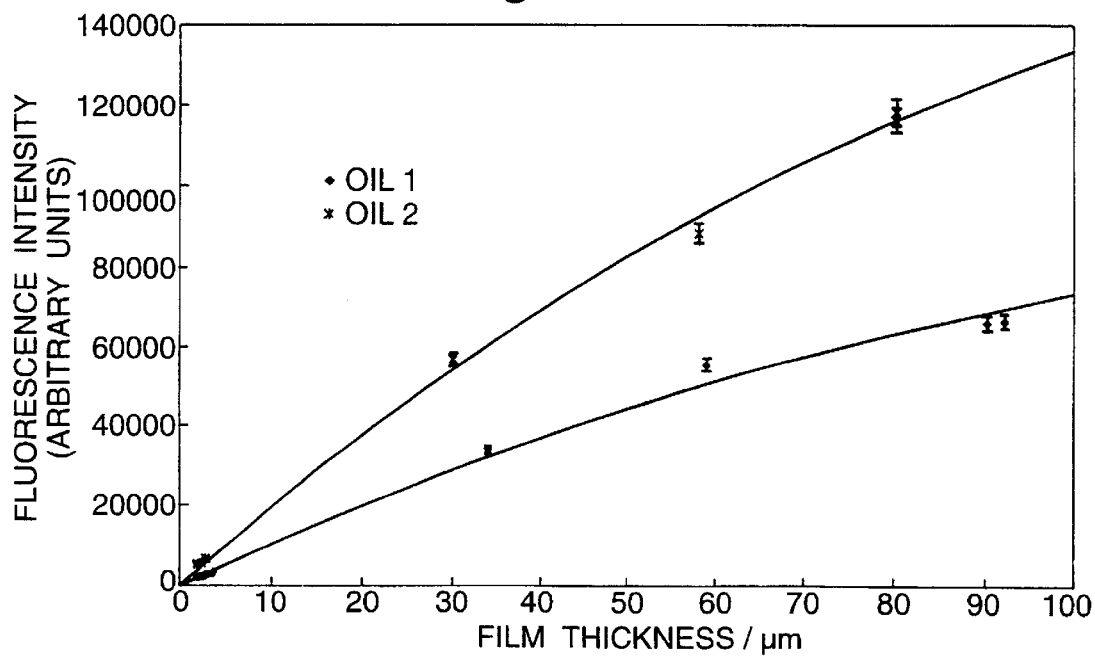
FIG. 2 shows graphically how the intensity of the fluorescent light varies with oil film thickness, for two different oils.

Referring now to FIG. 2, the intensity, I, of the fluorescent light increases with the thickness, l, of the oil film in the way that can be deduced from Beer-Lambert's law, such that:

$$I=A(1-e^{-Bl})$$

where A is an experimental scaling factor, and B depends on the oil. The values of B for oil 1 and oil 2 were $8.43\times10^{-3}$ $\mu m^{-1}$ and $9.78\times10^{-3}$ $\mu m^{-1}$ respectively. These results are at room temperature, and are determined from plots such as FIG. 2.

Figure 3:
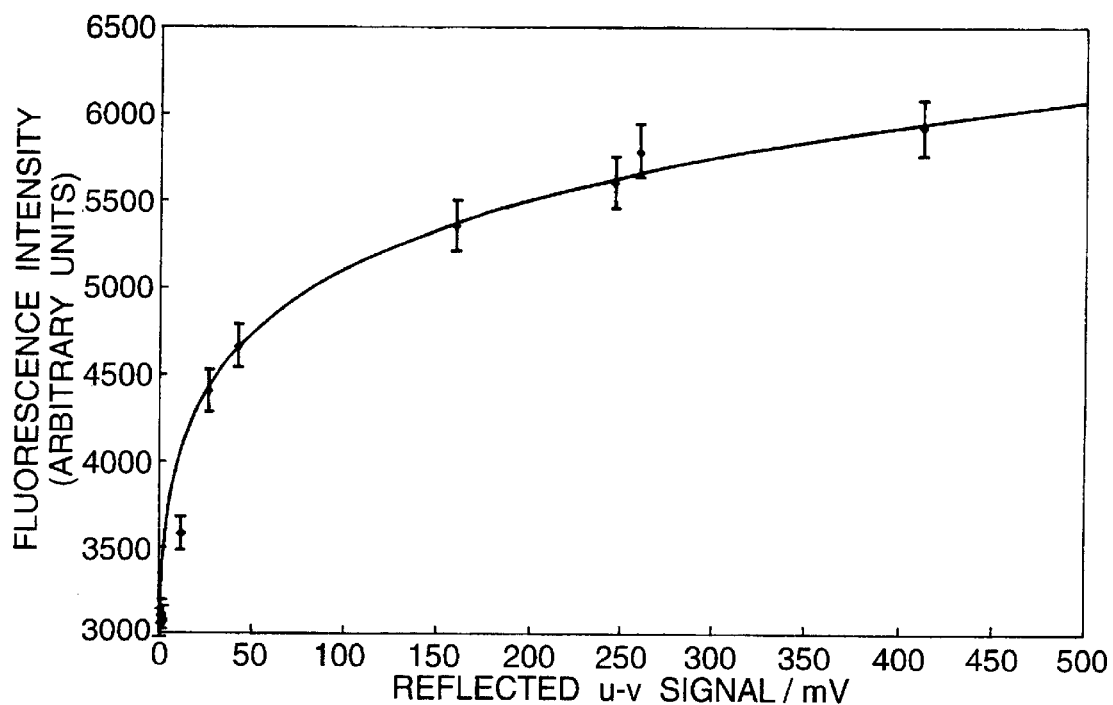
FIG. 3 shows graphically how the intensity of the fluorescent light varies with the intensity of the reflected radiation (for oil 2)

When the sheet 12 is moving, the reflectivity cannot be assumed to be constant; and the reflectivity affects not only the intensity of the fluorescent light (measured by the detectors 44 and 48), but also the intensity of the scattered u-v (measured by detector 38). Referring now to FIG. 3, this shows how the fluorescent light intensity varies with the reflected u-v signal for a 1 $\mu m$ thick film of oil 2. Very similar curves have been found with other oils, and they all fit the equation:

$$I=G(1+3\rho^z)$$

where $\rho$ is the proportion of the u-v radiation which is reflected, G a scaling factor and z found empirically to be about 0.3.

Hence the intensity of the fluorescence can be corrected for changes in reflectivity, if the reflectivity is measured independently. In the apparatus 10 of FIG. 1 the reflectivity is monitored by focusing the light from a red LED 50 using a lens 52 onto the measurement point on the sheet 12. The LED output power is monitored using a beam splitter 54 and a detector 56, whilst the light reflected from the sheet 12 is monitored using a detector 58. The wavelength of the light is such that it experiences negligible absorption by the oil film on the sheet 12.

Measurement of the reflectivity in this way allows the reflected u-v radiation measured by detector 38 to be used to correct for experimental set up factors such as excitation energy and optics collection efficiency. The way this is done is outlined below.

The technique is based on relating intensities of fluorescence to oil film thickness and so careful calibration must be carried out. An initial calibration signal is collected from a fluorescent marker placed at the measurement position at a known temperature. This marker should be selected to have a fluorescence equivalent to a given oil film thickness; and should be optically thin so that the reflection of light from the substrate surface can be recorded. For example the fluorescence from a 1 mm thick layer of a 1.6 mM solution of pyrene in dodecane is equivalent to that from a film of oil 1 about 4 $\mu m$ thick. The fluorescent light and reflected radiation from this marker are collected through the same optical system and recorded separately. At the same time, the output and reflected light (from the probed sample position) of the reference beam that is not absorbed by the marker or oil is recorded. By then monitoring these same quantities when taking sample measurements, changes in surface reflectivity, incident u-v intensity, and coupling into the optical system can be accounted for and the fluorescent light can be quantitatively related to oil film thickness. This is outlined in the equations below.

The amount of light transmitted, $I_1$, through a film of thickness l is given by $$I_1=I_0 e^{-Bl}$$

where $I_0$ is the initial excitation light intensity, and B is a constant. The amount of light absorbed is given by $I_0-I_1$, and the fluorescence intensity, I, is proportional to the amount of light absorbed, so that $$I=KI_0(1-e^{-Bl})$$

where K accounts for experimental factors such as collection efficiency, etc.

Hence, as discussed earlier $$I=A(1-e^{-Bl})$$

where A is an experimental scaling factor, and B depends on the absorption characteristics of the oil. However, in this application the film is usually adhering to a reflective surface which will alter the amount of light observed, because of reflection of both excitation (u-v) and fluorescent light. Laboratory experiments have shown that the fluorescence observed is empirically modified as follows:

$$I = A(1 - e^{-Bl})\left(1 + 3\times\left(\frac{R_1}{R_0}\right)^z\right)$$

where $R_0$ and $R_1$ are the intensities of the incident and reflected u-v radiation. The value of z has been found to be the same (~0.3) for all oils studied, but its precise value may depend on the collection method of the reflected light.

Rearranging this equation leads to an expression for calculating film thickness from fluorescence intensity:

$$l = \frac{-1}{B}\text{Ln}\left(1 - \frac{1}{A(1 + 3\times(R_1/R_0)^z)}\right)$$

The experimental factor, A, can be initially determined by measuring the fluorescence from the standard calibration solution at a known temperature. The value of B is that for the oil to be investigated (pre-determined in laboratory experiments). The reflectivity of the surface $R_1/R_0$, is desirably replaced in the above equation by $S_1/S_0$ where the $S_0$ and $S_1$ are the intensities of the incident and reflected radiation with the light from the reference source 50, as this is less likely to be affected by any changes in optical coupling.

The parameter A, ideally a constant, is desirably replaced by $A_x f_t$ where $f_t$ is a factor to account for the different temperature the oil is at compared to the calibration experiment. Its value is calculated from laboratory experiments measuring the oil fluorescence as a function of temperature. The temperature is determined using the ratio of two oil fluorescence wavelengths. If the measurements are at the same temperature as the calibration, $f_t=1$. $A_x$ is the new experimental factor that may have changed from the initial calibration experiment due to variations in excitation energy, collection efficiency, etc. it is related to the original factor by $$A_x = A \left( \frac{R_1}{R_1^*} \right) \left( \frac{S_1^* / S_0^*}{S_1 / S_0} \right)$$

where the asterisked values are those measured with the standard calibration solution. So, after the initial calibration the system is effectively continuously internally calibrated relative to the initial calibration experiment, to give accurate film thicknesses.

This method has been shown to be able to measure thicknesses of less than 0.1 μm, and to be accurate to within 10%.

What is claimed is:

1. A method of monitoring the thickness of oil on a surface of metal substrate comprising the steps of illuminating a region of the surface with radiation of a suitable wavelength to cause fluorescence in the oil, and detecting the intensity of the fluorescent radiation, characterized by also illuminating the same region of the surface at the same time with a reference beam that experiences negligible absorption when incident on the oil, and measuring the intensity of the reflected reference beam to provide a measure of the reflectivity of the surface, and determining the thickness of the oil at that region from both the values of the fluorescent intensity and the reflectivity of the surface.

2. A method as claimed in claim 1 including the step of measuring the intensity of reflected radiation originating from the fluorescence-causing illumination.

3. A method as claimed in claim 1 including the step of directing the reference beam to be incident substantially along a normal to said surface.

4. A method as claimed in claim 1 including the steps of providing the fluorescence-causing illumination in brief flashes, and gating the means detecting the fluorescent radiation to operate in synchronism with said flashes.

5. A method as claimed in claim 1 including the step of measuring the intensity of fluorescent radiation at two different wavelengths for enabling changes of temperature to be taken into account.

6. A method of monitoring the thickness of oil on a surface of metal substrate, comprising the steps of illuminating a region of the surface with radiation of a suitable wavelength to cause fluorescence in the oil, and detecting the intensity of the fluorescent radiation, characterized by also measuring the intensity of radiation reflected from the same region of the surface to provide a measure of the reflectivity of the surface, and determining the thickness of the oil at that region from both the values of the fluorescent intensity and the reflectivity of the surface, wherein the intensity of the fluorescent radiation is measured at two different wavelengths in order to enable changes of temperature to be taken into account.

7. A method as claimed in claim 6 including the step of measuring the intensity of reflected radiation originating from the fluorescence-causing illumination.

8. A method as claimed in claim 7 including the steps wherein the same region of the substrate is also illuminated with a reference beam that experiences negligible absorption when incident on the organic material, and measuring the intensity of the reflected reference beam.

9. A method as claimed in claim 8 including the step of directing the reference beam to be incident substantially along a normal to the surface.

10. A method as claimed in claim 6 including the steps of providing the fluorescence-causing illumination in brief flashes and the gating the means detecting the fluorescent radiation to operate in synchronism with said flashes.

11. An apparatus for monitoring the thickness of oil on a surface of a metal substrate, said apparatus comprising means for illuminating a region of said surface with radiation of a suitable wavelength to cause fluorescence in the oil, means for detecting the intensity of the fluorescent radiation and providing a signal representative thereof, means for illuminating the same region of the substrate at the same time with a reference beam that experiences negligible absorption when incident on said oil, means for measuring the intensity of the reflected reference beam for providing a signal representing the said intensity of reflected radiation to provide an indication of the reflectivity of said surface, and means for calculating the thickness of said oil at that region from signals representing the value of the fluorescent intensity and the reflectivity of said surface.

12. An apparatus for monitoring the thickness of oil on a surface of a metal substrate, said apparatus comprising means for illuminating a region of said surface with radiation of a suitable wavelength to cause fluorescence in the oil, means for detecting the intensity of the fluorescent radiation and providing a signal representative thereof, means for measuring the intensity of radiation reflected from the same region of the surface, for providing a signal representing the intensity of the reflected radiation to provide an indication of the reflectivity of the surface, and means for calculating the thickness of the oil at said region from signals representing the value of the fluorescent intensity and the reflectivity of the surface, wherein said means for detecting the intensity of the fluorescent radiation incorporates means for determining the intensity at two different wavelengths, and hence to take into account the temperature of said oil.

* * * * *